United States Patent [19]

Ishikawa et al.

[11] Patent Number: 4,683,198
[45] Date of Patent: Jul. 28, 1987

[54] NOVEL MALTOSE DEHYDROGENASE, PROCESS FOR ITS PRODUCTION, AND ANALYTICAL METHOD USING THE SAME

[75] Inventors: Hidehiko Ishikawa; Kazuo Matsuura; Hideo Misaki, all of Shizuoka, Japan

[73] Assignee: Toyo Jozo Kabushiki Kaisha, Shizuoka, Japan

[21] Appl. No.: 674,009

[22] Filed: Nov. 23, 1984

[30] Foreign Application Priority Data

Nov. 22, 1983 [JP] Japan ................... 58-219792

[51] Int. Cl.$^4$ .......................... C12Q 1/40; C12N 9/04
[52] U.S. Cl. ........................................ 435/22; 435/26; 435/190; 435/882; 435/883; 435/884
[58] Field of Search ................... 435/22, 26, 190, 882, 435/883, 884

[56] References Cited

U.S. PATENT DOCUMENTS

| 3,806,416 | 4/1974 | Mollering | 435/195 |
| 4,385,112 | 5/1983 | Misaki et al. | 435/6 |
| 4,427,771 | 1/1984 | Misaki et al. | 435/22 |

FOREIGN PATENT DOCUMENTS

| 0112973 | 6/1984 | Japan | 435/26 |
| 2088052 | 6/1982 | United Kingdom . | |

OTHER PUBLICATIONS

Kobayashi et al., Agric. Biol. Chem. 46(8), 2139-2142, (1982).
Enzyme Handbook, pp. 19, 42, 43: 1.1.1.46, 1.1.1.47, 1.1.1.116–1.1.1.120.
Membrane-Bound D-Glucose Dehydrogenase from Pseudomonas sp.: Solubilization, Purification and Characterization, Agricultural Biological Chemistry, vol. 44(7), 1980, pp. 1505-1512.
D-Glucose Dehydrogenase of Gluconobacter Suboxydons: Solubilization, Purification and Characterization, Agricultural Biological Chemistry, vol. 45(4), 1981, pp. 851-861.

Primary Examiner—Christine M. Nucker
Attorney, Agent, or Firm—Young & Thompson

[57] ABSTRACT

An enzyme which acts on a reducing terminal of a monosaccharide or oligosaccharide without requiring NAD or NADP and which catalyzes the reaction

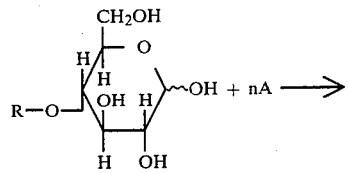

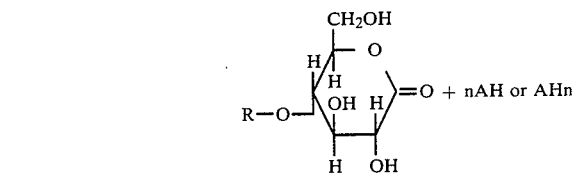

wherein R is a saccharide chain residue or hydrogen, A is a hydrogen acceptor other than NAD or NADP, AH or AHn is a reduced form acceptor and n is 1 or 2. This maltose dehydrogenase is produced by culturing a microorganism belonging to genus Staphylococcus, specifically, sp. B-0875 FERM BP-385, and isolating the thus-produced maltose dehydrogenase from the culture medium. An assay method for the determination of saccharide or the activity of a saccharide liberating enzyme, comprises reacting this enzyme with a substrate in the presence of a hydrogen acceptor, and measuring the amount of a detectable change.

22 Claims, 17 Drawing Figures

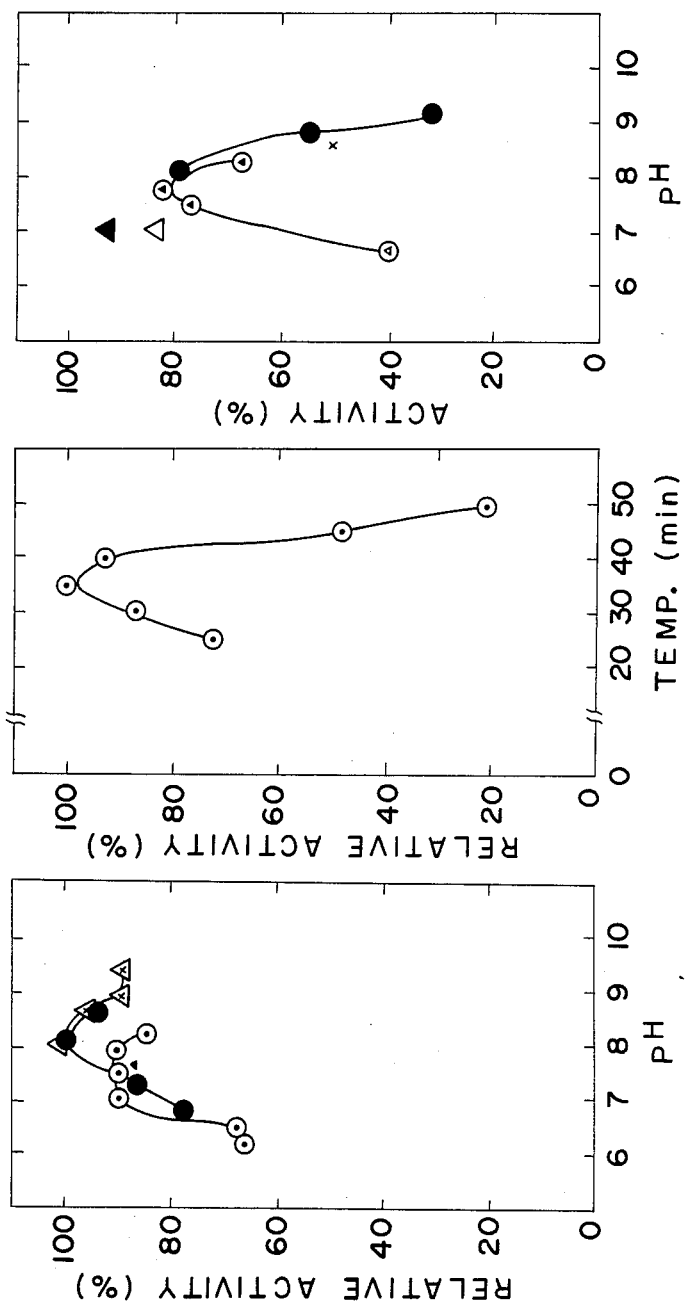

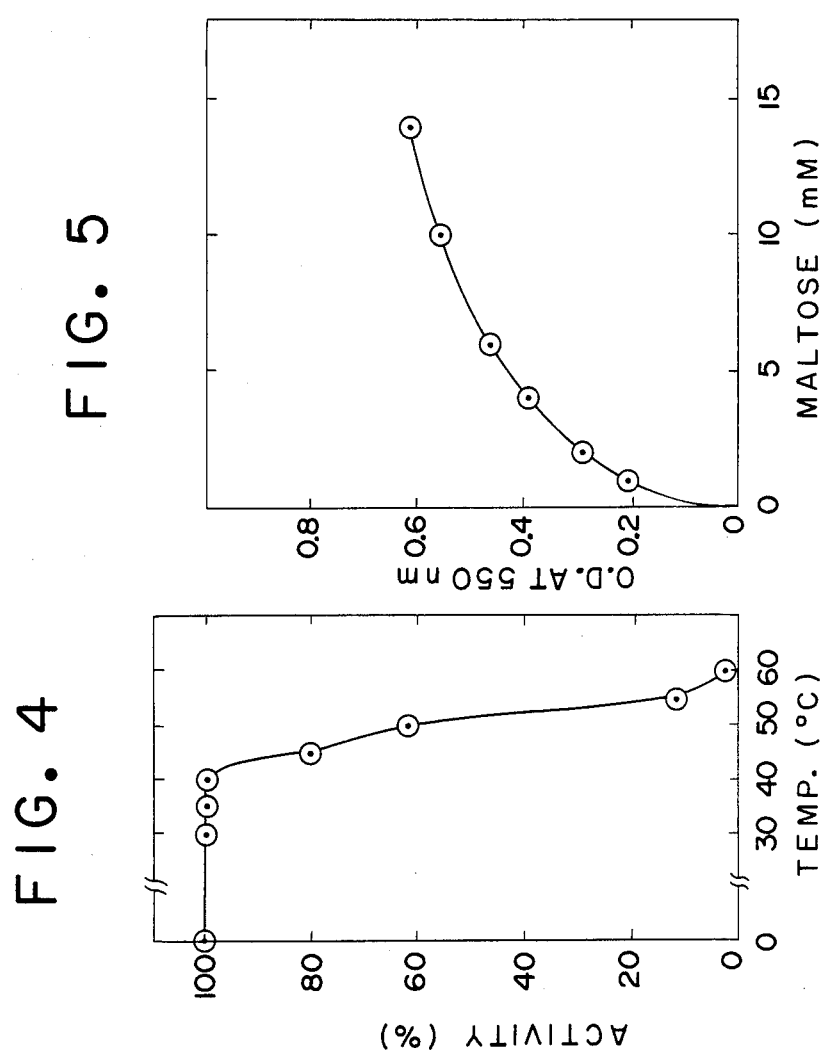

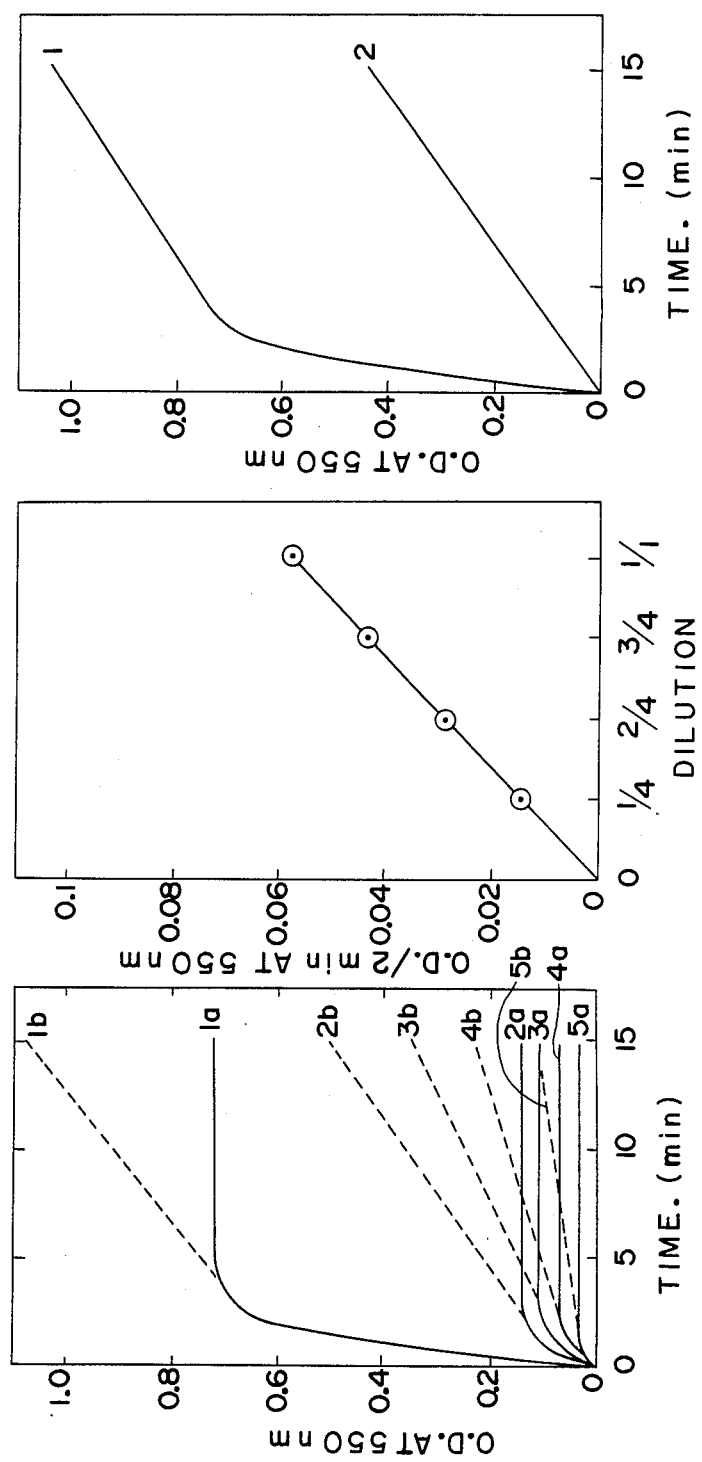

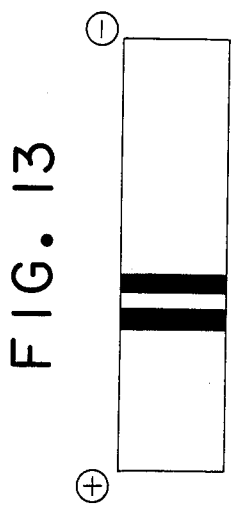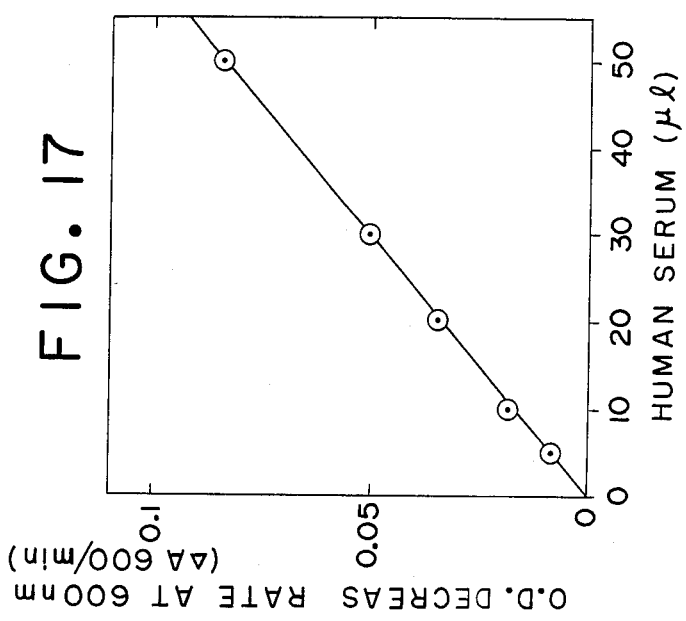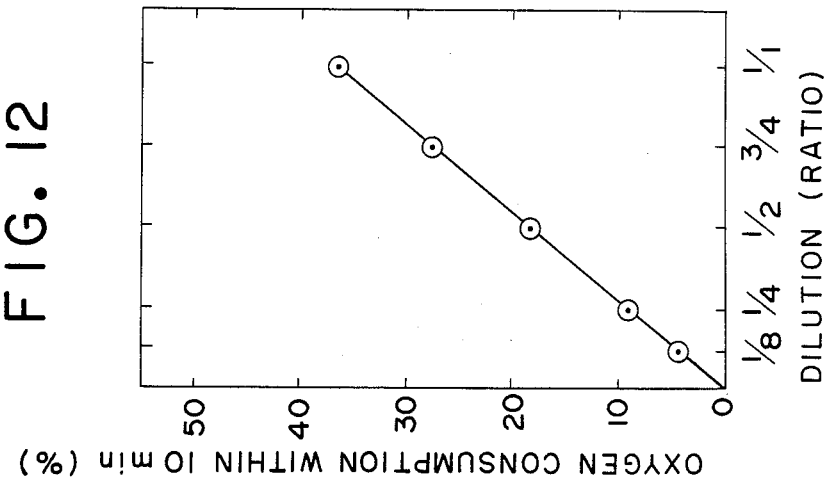

NOVEL MALTOSE DEHYDROGENASE, PROCESS FOR ITS PRODUCTION, AND ANALYTICAL METHOD USING THE SAME

This invention relates to novel maltose dehydrogenase, a process for its production, and an analytical method using the same. More particularly, the present invention pertains to a novel enzyme which acts on a reducing terminal of a monosaccharide or oligosaccharide without requiring NAD (nicotine adenine dinucleotide) or NADP (nicotine adenine dinucleotide phosphate) and which catalyzes the reaction

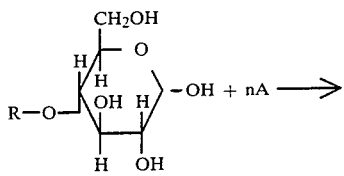

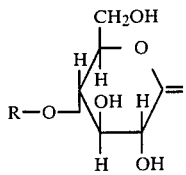

wherein R is a saccharide chain residue or hydrogen, A is a hydrogen acceptor other than NAD or NADP, AH or ANn is a reduced form acceptor and n is 1 or 2; and a process for the production of the said enzyme, which comprises culturing a microorganism producing the enzyme, said microorganism belonging to genus Staphylococcus, and isolating the thus-produced said enzyme therefrom, and an assay method for the determination of saccharide or an activity of a saccharide-liberating enzyme, which comprises reacting the above enzyme with a substrate in the presence of a hydrogen acceptor, and measuring the amount of detectable change.

Heretofore, various kinds of dehydrogenase, an enzyme which acts on a reducing terminal of a monosaccharide or oligosaccharide and catalyzes a dehydrogenation reaction in the presence of a hydrogen acceptor, such as glucose hydrogenase [EC. 1.1.1.47 glucose dehydrogenase (Enzyme Handbook, p. 19, December 1982), EC. 1.1.1.118 glucose dehydrogenase (NAD+) (ibid., p. 42), EC. 1.1.1.119 glucose dehydrogenase (NADP+) (ibid., p. 43)] or maltose dehydrogenase (British Patent Publ. 2,088,052 A) have been known. These enzymes require NAD or NADP as a hydrogen acceptor. Furthermore, an enzyme which does not utilize NAD or NADP but utilizes phenazine methosulfate (PMS) and oxidizes (dehydrogenation) glucose, for example an enzyme produced by Pseudomonas sp. or Gluconobacter suboxydance is known. [Matsushita et al., Agr. Biol. Chem., 44, 1505-1512 (1980), ibid., 45, 851-861 (1981)]. These known enzymes have shown activity on glucose, but have shown less activity on oligosaccharides larger than maltose.

We have found that the strain No. B-0875 belonging to genus Staphylococcus, isolated from a soil sample obtained from a potato field in Oaza-moriuchi, Iwakuni-shi, Yamaguchi-ken, Japan, produces a novel enzyme [hereinafter designated as maltose dehydrogenase (acceptor)] which acts on a reducing terminal of a monosaccharide or oligosaccharide, requiring no NAD or NADP as cofactor but requiring PMS, 1-methoxy-phenazine methosulfate (MPMS) or meldola blue (9-dimethylaminobenzophenazoxonium chloride) as a hydrogen acceptor, showing greater activity on maltose than glucose (in contrast to prior known glucose dehydrogenases) having also substrate specificity on maltotriose, maltotetraose, maltopentaose and maltohexaose, and which catalyzes the reaction

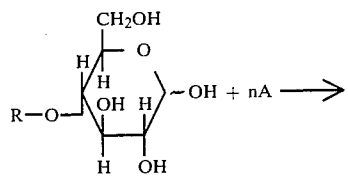

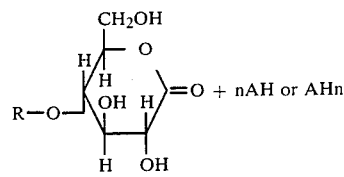

wherein R is a saccharide chain residue or hydrogen, A is a hydrogen acceptor other than NAD or NADP, AH or ANn is a reduced form acceptor and n is integer of 1 or 2.

We have also found that a determination of saccharide or the assay of an enzyme which liberates saccharide can advantageously be performed in the presence of a hydrogen acceptor, by using the present maltose dehydrogenase (acceptor).

The taxonomical properties of the maltose dehydrogenase (acceptor) producing microorganism are as follows:

1. Morphological characteristics:
   Observed on a nutrient agar* cultured at 30° C. for 18 hours.
   *peptone 10 g, meat extract 5 g, NaCl 3 g, dist. water 1000 ml, pH 7.2
   (1) Shape, size and polymorphism of cells: Mainly in pairs, or single, short chains and flocculent cocci. No polymorphism. Size 0.6–1.0 μm.
   (2) Motility and flagella: none
   (3) Spores: none
   (4) Gram stain: positive (easily decolored)
   (5) Acid-fast stain: negative
2. Growth characteristics:
   (1) Bouillon agar plate medium (30° C., 18 hours) and nutrient agar plate medium: colonies; convex, round and smooth edges. Creamy white or grayish white. No soluble pigment formation.
   (2) Bouillon agar slant (30° C., 18 hours) and nutrient agar slant: good growth with linear growth. Grayish white-creamy white. No soluble pigment formation.
   (3) Bouillon broth (30° C., 18–42 hours): good growth with uniform turbidity. Forms thin pellicle.
   (4) Litmus milk or BCP milk: acidic coagulation within 2 weeks culture, partial peptonization.
3. Physiological properties:

| | |
|---|---|
| Nitrate reduction | − |
| Denitrification reaction | − |
| MR-test | − |
| VP-test | − |
| H₂S formation | − |
| Starch hydrolysis | + (weak) |

-continued

| Citrate utilization | |
|---|---|
| (Simons medium) | + |
| (Christenssen medium) | + |
| Nitrate utilization | − |
| Ammonium utilization | + |
| Pigment formation | − |
| Urease (SSR) | − |
| (Christenssen) | + |
| Oxidase | − |
| Catalase | + |
| Growth (pH) | 5-9 |
| (temp.) | 10-37° C. |
| Nature | aerobic |
| OF-test | |
| (Hugh-Leifson medium*) | 0 (weak acid formation under anaerobic conditions after 2-3 weeks culture) |
| (non-peptonic medium**) | 0 |
| Gelatin liquefaction | − |
| Caseine hydrolysis | − |
| Arginine decomposition | + |
| Lysine decarboxylation | not test |
| Resistant to NaCl | up to 5% |
| Growth on FTO medium | − |
| GC % (Tm-method) | 39% |

*Hugh-Leifson medium: peptone 2.0 g, NaCl 5.0 g, $K_2HPO_4$ 0.3 g, Bromthymol blue (0.2%) 10.0 ml, dist. water 1000 ml, agar 3.0 g, pH 7.2
**Non-peptonic medium: $NH_4H_2PO_4$ 1.0 gm, KCl 0.2 g, $MgSO_4 \cdot 7H_2O$ 0.2 g, yeast extract 1.0 g, agar 3.0 g, BTB (0.2%) 10.01 ml, dist. water 1000 ml, pH 7.2

4. Acid or gas formation from sugar (basal medium: Hugh-Leifson medium and non-peptonic medium; same results were obtained)

TABLE 1

| Sugar | Acid | Gas | Sugar | Acid | Gas |
|---|---|---|---|---|---|
| adonitol | − | − | D-mannitol | − | − |
| L-arabinose | + | − | D-mannose | + | − |
| cellobiose | + | − | melezitose | − | − |
| dulcitol | − | − | melibiose | + | − |
| meso-erythritol | − | − | raffinose | − | − |
| D-fructose | − | − | L(+)rhamnose | + | − |
| fucose | + | − | D-ribose | + | − |
| D-galactose | + | − | salicine | − | − |
| D-glucose | + | − | L-sorbose | − | − |
| glycerin | − | − | sorbitol | − | − |
| inositol | − | − | starch | − | − |
| inulin | − | − | saccharose | − | − |
| lactose | + | − | treharose | − | − |
| maltose | − | − | D-xylose | + | − |

Summarizing the principal features of the strain hereinabove, the strain is generally formed in pairs, occasionally single, short-linked chains or flocculent Gram positive cocci (easily decolorized), non-motile aerobic bacteria with no polymorphism. The strain is positive in catalase, and negative in oxidase, oxidative decomposition of sugars and acid formation. Sometimes it shows F in the OF-test upon more than 3 weeks culture in a medium, in which ammonium phosphate is removed from the non-peptonic medium, and a weak acid is formed under anaerobic conditions. The guanine-citocine content (GC%) is 39%.

Consulting *Bergey's Manual of Determinative Bacteriology*, 8th Ed. (1974), the present strain is seen to belong to Micrococcuceae, genus Micrococcus, genus Staphylococcus, genus Planococcus and genus Stomatococcus have been reported. According to the morphological propertirs (motility) and biochemical properties (OF-test), the strain seems to belong to genus Micrococcus; however, the GC% of genus Micrococcus is known to be 66-75%, which differs by more than 25% from the present strain. Since the difference in GC% indicates a great difference from a genetic polymorphism and phylogenetic point of view, the present strain cannot belong to genus Micrococcus. In a facultative anaerobe, genus Staphylococcus (generally, OF-test:, F, GC%: 30-40%), a mutant which effects the oxidative decomposition of sugar has been reported (Int. J. Sys. Bacteriol., 26: 22-37, 1976). The present strain B-0875 is identified as belonging to genus Staphylococcus on the basis of its characteristic GC% of 39%, formation of weak acid under anaerobic (fermentative) conditions for long term culture (3 weeks) in OF-test, namely F in OF-test, and no growth properties in FTO agar medium (refer to *The Prokaryotes*, Vol. II, 1981). The present strain is referred to as Staphylococcus sp. B-0875 and the strain has been deposited in The Fermentation Institute, Agency of Industrial Science and Technology, M.I.T.I. as deposition No. FERM BP-385 according to the Budapest Treaty.

Maltose dehydrogenase (acceptor) of the present invention can be obtained by culturing the maltose dehydrogenase (acceptor) producing microorganism of the present invention in a conventional medium for antibiotic or enzyme production. Cultivation can be carried out in solid or liquid medium. Submerged aeration culture is preferable for industrial production. Nutrient sources for the medium are conventional media for microorganism cultivation. Nutrient sources are assimilable nitrogen sources such as corn steep liquor, peptone, casein, soybean powder, yeast extract or meat extracts. Carbon sources are assimilable carbon sources such as molasses, glucose, glycerol, surcrose or dextrin. Inorganic salts such as sodium chloride, potassium chloride, magnesium sulfate, potassium dihydrogen phosphate or potassium hydrogen phosphate may be added. The culturing temperature can be varied depending on the growth of microrganisms and maltose dehydrogenase (acceptor) production, and is preferably 25°-30° C. The culturing time depends on the conditions and is usually 15-72 hours. Culturation should be terminated at the stage of maximum production of the enzyme. Maltose dehydrogenase (acceptor) of the present invention is contained in the cultured cells.

An example of the enzyme extraction is that isolated cultured wet cells are treated with lysozyme in a tris-HCl buffer, with sonication or the French-press treatment to obtain a crude maltose dehydrogenase (acceptor) solution. The crude enzyme solution is treated by known enzyme isolation and purification procedures to obtain the purified enzyme. Organic solvent precipitation such as with acetone, methanol or ethanol, or salting out with ammonium sulfate, sodium chloride or aluminum sulfate can be used. Further purification can be achieved by adsorption chromatography using an ion-exchanger such as carboxymethyl cellulose, carboxymethyl-dextran gel or sulfopropyl-dextran gel, or a gel-filtration agent such as dextran gel or polyacrylamide gel, with lyophilization to obtain the purified maltose dehydrogenase (acceptor) powder.

An assay method and the biochemical properties of the thus-obtained maltose dehydrogenase (acceptor) are as follows:
1. Assay method:
   20 mM phosphate buffer (pH 7.5)
   0.1% bovine serum albumin
   0.025% nitrotetrazolium blue (NTB)
   0.2% Triton X-100
   0.001% phenazine methosulfate (PMS: hydrogen acceptor)
   0.1M maltose The above reaction mixture (1.0 ml) in a small test tube is pre-incubated at 37° C. Enzyme solution (10 μl) is added thereto and incubated at 37° C. for 10 min. The reaction is stopped by adding 0.1N HCl (2.0 ml) and the optical density at 550 nm (As) is measured. Distilled water (10 μl) is added as a control and the amount measured at 550 nm (Ab).

One unit is defined by the amount of enzyme which oxidizes (dehydrogenates) 1 μmole of maltose in one minute and enzyme activity is calculated by the following equation:

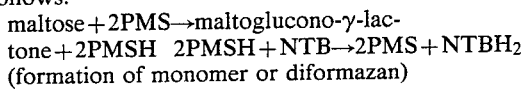

$$\text{activity (unit/ml)} = \frac{(As - Ab) \times 3.01}{12.4 \times 10 \times 0.01}$$

The enzymatic reaction of the above may be shown as follows:

maltose+2PMS→maltoglucono-γ-lactone+2PMSH 2PMSH+NTB→2PMS+NTBH₂ (formation of monomer or diformazan)

2. Substrate specificity:

Maltose in the above assay method is replaced by the substrates in Table 2 (each 0.1M, 0.1 ml) and assayed according to the above assay method.

TABLE 2

| Substrate | Relative activity (%) |
|---|---|
| maltose | 100 |
| xylose | 53.7 |
| glucose | 80.0 |
| galactose | 56.1 |
| mannose | 52.4 |
| fructose | 31.4 |
| sucrose | 0 |
| lactose | 58.2 |
| raffinose | 0 |
| maltotriose | 77.4 |
| maltotetraose | 60.3 |
| maltopentaose | 36.4 |
| maltohexaose | 28.6 |
| maltoheptaose | 22.4 |
| dextrin (mol. weight more than 1700) | 11.0 |
| inositol | 0 |
| sorbitol | 0 |
| glycerol | 0 |
| ethanol | 0 |

As shown in Table 2, the enzyme of the present invention has substrate specificity on maltose and also on oligosaccharides such as glucose, maltotriose, maltotetraose, maltopentaose, maltohexaose, maltoheptaose and dextrin.

3. Hydrogen acceptor (A):

Hydrogen acceptor (coenzyme) of maltose dehydrogenase (acceptor) in the oxidative reaction (dehydrogenation) of maltose is measured according to the assay method. The results are shown in Table 3. Maltose dehydrogenase (acceptor) of the present invention requires no NAD or NADP as a coenzyme. A decrease in soluble oxygen is observed at least whwn PMS, 1-methoxy-phenazine methosulfate (MPMS) or meldola blue is used as a hydrogen acceptor. Furthermore, 1-acetamide-phenazine methosulfate, and 2,6-dichloro-phenolindophenol and a phenolindophenol such as a phenolindophenol-group compound can also be a hydrogen acceptor.

The reaction may be illustrated as follows:
maltose+2PMS→maltogluconolactone+2PMSH
2PMSH+½O₂→2PMS+H₂O Furthermore, the following reaction can be estimated:

maltose+nA→maltogluconolactone+nAH (or AHn)

TABLE 3

| Hydrogen acceptor | Reaction pH | Relative Activity (%) | O₂ Consumption |
|---|---|---|---|
| NAD | 7.5 | 0 | — |
| NADP | 7.5 | 0 | — |
| PMS | 7.5 | 100 | + |
| MPMS | 7.5 | 30 | + |
| meldola blue | 7.5 | 20 | + |
| methylene blue | 7.5 | 0 | — |
| ferricyanide | 7.5 | 0 | — |
| NTB | 7.5 | 0 | — |

4. Enzyme action:

The enzyme catalyzes the reaction

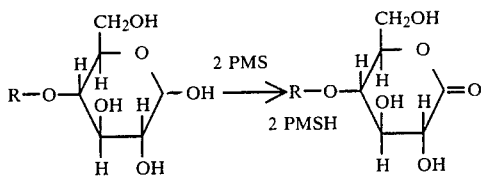

wherein R is a saccharide chain residue or hydrogen.

As shown, the enzyme catalyzes a dehydrogenation reaction in which a reducing terminal or a substrate such as glucose or an oligosaccharide is dehydrogenated in the presence of a hydrogen acceptor such as PMS to form an oxidized substrate.

5. Optimum pH:

The 20 mM phosphate buffer solution (pH 7.5) in the assay method hereinbefore is replaced by other buffer solutions and the effect of pH on the enzyme is measured. The results are shown in FIG. 1, wherein ⊙-⊙: 0.2M phosphate buffer (pH 6.4-8.4) ●-●: 0.2M Tris-HCl buffer (pH 6.8-8.7), △-△: glycine-NaOH buffer (pH 8.0-9.4).

6. Optimum temperature:

Reaction mixture (1.0 ml) as in the assay method hereinabove is heated at various temperatures in the range 25°-50° C. for 3 minutes. Enzyme solution (0.2 U/ml, 0.02 ml) is added thereto, and the mixture is incubated at the temperature in question for 10 minutes. 0.1N HCl (2.0 ml) is added to stop the enzyme reaction, and then the increased amount of PMSH₂ is measured by optical density at 550 nm. The results are shown in FIG. 2. The optimum temperature of maltose dehydrogenase (acceptor) of the present invention is approximately 35° C.

7. pH stability:

A mixture of enzyme solution (10 U/ml, 0.1 ml), a number of buffer solutions (0.1 ml, each at a different pH) and distilled water (0.8 ml) is pre-incubated at 37° C. for 60 minutes. The reaction mixture is immediately cooled in ice water and enzyme activity is assayed according to the above assay method. The results are shown in FIG. 3. In the figure, O-O: Tris-HCl buffer (pH 6.6-8.3), ●-●: glycine-NaOH buffer (pH 8.1-9.2),: △TES buffer (pH 7.0), and: ▲BES buffer (pH 7.0). The optimum pH stability of maltose dehydrogenase (acceptor) of the present invention is at pH 7.5-8.5 at 37° C. for 60 minutes treatment and stabilized by Good's buffer.

8. Heat stability:

A mixture of enzyme solution (10 U/ml, 0.1 ml), 0.2M BES buffer (pH 7.0, 0.1 ml) and distilled water (0.8 ml)

is preincubated at various temperatures in the range 30°–60° C. for 10 min. After treatment, the reaction mixture is cooled in ice water, and then the enzyme activity of the mixture is assayed according to the above assay method. The results are shown in FIG. 4. Maltose dehydrogenase (acceptor) of the present invention has heat stability below 40° C. at pH 7.5 for 10 minutes treatment.

9. Molecular weight:

80,000±10,000 (gel-filtration method using Sephacryl S-200 (trademark)).

10. Iso-electric point:

Approximately pH 9.5 (electrophoresis using carrier ampholite).

11. Km value:

The substrate (maltosel $\alpha$ and $\beta$ mixture) concentration-reaction rate relation is shown in FIG. 5. Under the experimental conditions, Vmax cannot be determined and no linear Lineweaver-Burk plot can be obtained. Therefore, the correct Km value cannot be determined, and the approximate Km value is calculated according to FIG. 5 as approximately 3.8 mM, and the Km value for $\beta$-maltose is calculated as 1.36 mM.

12. Effect of metallic ions, EDTA and KCN:

Metallic ions, EDTA or KCN shown in Table 4 is added to the reaction mixture as in the assay method, and the effect thereof is measured. The results are shown in

TABLE 4

| Additives | Relative Activity (%) | Additives | Relative Activity (%) |
|---|---|---|---|
| No addition | 100 | 1.0 mM CoCl$_2$ | 17.9 |
| 1.0 mM LiCl | 95 | 1.0 mM ZnCl$_2$ | 4.5 |
| 1.0 mM CaCl$_2$ | 101 | 1.0 mM CuCl$_2$ | 0 |
| 1.0 mM MgCl$_2$ | 106 | 1.0 mM NaN$_3$ | 95 |
| 1.0 mM BaCl$_2$ | 61.2 | 1.0 mM KCN | 95 |
| 1.0 mM MnCl$_2$ | 13.4 | 5.0 mM EDTA | 73 |

13. Effect of surface-active agents:

Surface active agents as in Table 5 are added one at a time to aliquots of the reaction mixture as in the assay method, in place of 0.2% Triton X-100, and the enzyme activity is measured. The results are shown in Table 5.

TABLE 5

| Surface Active Agent | Concentration (%) | Relative Activity (%) |
|---|---|---|
| No addition | — | 100 |
| Cation PC-8 | 0.1 | 107 |
| Cation FB | 0.1 | 96 |
| Cation DT-205 | 0.1 | 111 |
| Sarcosinate PN | 0.1 | 114 |
| Sodium laurylbenzene sulfate | 0.1 | 0.2 |
| SDS | 0.1 | 3.8 |
| Briggi 35 | 0.1 | 106 |
| Tween-80 | 0.1 | 104 |
| Nikkol-OP-10 | 0.1 | 104 |
| Span-85 | 0.1 | 103 |
| Adekatol-SO-145 | 0.1 | 103 |
| Adekatol-SO-120 | 0.1 | 120 |
| Triton X-100 | 0.1 | 115 |
| Sodium cholate | 0.1 | 86 |
| Cetyl trimethylammonium chloride | 0.1 | 94 |

The novel maltose dehydrogenase (acceptor) of the present invention can be used for various kinds of assays based on its substance specificity and enzyme action. For example, in an assay of amylase activity, oligosaccharides generated from starch by the action of amylase are treated by the present maltose dehydrogenase (acceptor) in the presence of a hydrogen acceptor such as PMS, and the thus-generated reduced PMS is directly measured or the formazan pigment formed after the reaction with tetrazolium salt is colorimetrically measured. Therefore, the enzyme of the present invention is useful as a clinical diagnostic enzyme.

Furthermore, the present invention permits a quantitative determination of saccharides such as glucose and maltose and provides an assay method for enzymatic activity such as that of $\alpha$-amylase and $\beta$-amylase and glucoamylase in a specimen such as serum, saliva or urine, using the present maltose dehydrogenase (acceptor), which comprises decomposing the substrate such as a glucose polymer having a modified reducing terminal glucose residue or a cyclic glucose polymer, by the action of the novel maltose dehydrogenase (acceptor), and quantitatively measuring the decomposed substrate.

Hitherto known assay methods of amylase activity are based on the fact that a substrate glucose polymer such as starch is hydrolyzed by amylase action to form glucose, maltose or oligosaccharides. Examples are assay methods comprising measurement of the decrease of viscosity of starch by amylase action; iodometry; the reaction of glucose with glucose oxidase or glucose dehydrogenase and NAD (NADP), wherein glucose is formed by the action of $\alpha$-glucosidase on maltose which is produced from amylase action on starch; and the blue starch method or maltose phosphorylase method comprising colorimetrically measuring the soluble pigment produced by amylase action on insoluble pigment-bound starch (Jap. Pat. Publ. No. 55-27800).

Other methods are known, for example an assay method which comprises hydrolyzing a substrate such as p-nitrophenylmaltopentaoside, p-nitrophenylmaltohexaoside or p-nitrophenylmaltoheptaoside by the action of amylase, treating the generated p-nitrophenylmaltotriose or p-nitrophenylmaltoside with $\alpha$-glycosidase or $\beta$-glycosidase, and colorimetrically measuring the liberated p-nitrophenol.

These prior methods have a number of disadvantages, for example: variability of hydrolysis caused by the reagent used and the reaction conditions imposed, and the inhibitory action of coexisting glucose and maltose. Furthermore, in the blue starch method, a complicated separation procedure by centrifugation is required, which impedes automation, and in the maltose phosphorylase method, the four steps of enzyme treatment which are required render the operations expensive and difficult.

These prior assay methods have further disadvantages; for example, the amount of substrate hydrolyzed by the action of amylase or glycosidase cannot correctly be measured and is only proportional. However these earlier methods have been used because there was no practical alternative assay method.

We have found that saccharide-liberating enzyme activity can be assayed with simplicity and good accuracy, if the reducing terminal group of a glucose polymer having a reducing terminal glucose residue is esterified, etherified or oxidized to form a modified reducing terminal group which cannot be a substrate for maltose dehydrogenase (acceptor). The glucose polymer having a modified reducing terminal glucose residue thus produced, is then subjected to a substrate for assay of saccharide-liberating enzyme activity.

Furthermore, we have found that the said enzyme can advantageously be assayed if the glucose polymer having a modified reducing terminal glucose residue is replaced by a cyclic glucose polymer.

Further advantages are obtainable if the decomposed substrate produced in the enzymatic reaction is dehydrogenated by maltose dehydrogenase (acceptor) with hydrogen acceptor, and the thus-produced reduced maltose dehydrogenase (acceptor) is directly measured or indirectly measured by a hydrogen transport coloring reagent in reduced form, or the decreased amount of oxygen is measured.

Furthermore, in the present invention, when a substrate having a lower degree of polymerization on a saccharide such as a polymerization degree of 4–8 is used, accurate results can be obtained as one signal in one step.

Moreover, we have found that the enzymatic activity of a glycosidase such as amylase, glycosidase, glucoamylase, phosphatase or esterase in a specimen such as serum, saliva or urine can advantageously be assayed, without detrimental effects from a coexisting sugar such as glucose in the specimen, by previously or simultaneously treating the specimen with hexose oxidase, preferably glucose oxidase and catalase, or by treating the specimen with hexokinase in the presence of $Mg^{++}$ and ATP, or by pre-treating the specimen with maltose dehydrogenase (acceptor) in the presence of oxygen and a hydrogen acceptor.

It is accordingly an object of the present invention to provide an assay method of saccharide and saccharide-liberating enzyme activity, in which a substrate is treated with maltose dehydrogenase (acceptor) in the presence of a hydrogen acceptor, and the amount of a resulting detectable change is measured.

Another object of the present invention is to provide a determinative method of saccharide, or an assay method of a saccharide-liberating enzyme such as amylase or glycosidase.

Examples of substrates useful in the present invention are glucose polymers having modified reducing terminal glucose residues, oligosaccharides having a reducing terminal sugar chain which is not hydrolyzed by maltose dehydrogenase (acceptor), or cyclic glucose polymers, preferably of a polymerization degree above 1, most preferably above 4.

Examples of glucose polymers having modified reducing terminal glucose residues are maltotetraose, maltopentaose, maltohexaose, maltoheptaose, amylose, amylopectin, starch or starch hydrolyzates such as soluble starch (so-called dextrin) in which the reducing terminal glucose residue of the glucose polymer is modified.

The modified reducing terminal glucose residue of the present invention is a residue possessing no reducing activity, or a substrate other than for maltose dehydrogenase (acceptor).

Examples are etherified or esterified reducing terminal groups produced by conventional methods, or reducing terminals combined with fructose, inositol or sorbitol, or gluconic acid residues of oxidized glucose residues or their esterified derivatives.

Examples of these modifications are as follows:

A solution of polysaccharides such as soluble starch or dextrin is reacted with 4% methanolic hydrochloric acid at 70° C. for 4 hours, neutralized, and fractions collected having various degrees of polymerization by gel-filtration column chromatography to obtain methyl etherified oligosaccharides. The soluble starch is added to acetic anhydride (3.5 ml) in dry pyridine and reacted at 0° C. overnight. It is then precipitated by adding acetone, and fractions collected having various degrees of polymerization by gel-filtration column chromatography to obtain acetylated oligosaccharides.

Soluble starch in Fehling's reagent is boiled for 5 minutes to 20 hours, concentrated, the insolubles removed after addition of methanol and the fractions collected having various degrees of polymerization to obtain compounds in which the reducing terminal glucose residues are oxidized to gluconic acid residues which may be optionally esterified. Or carboxyl in a gluconic acid residue is reduced to an alcohol-type reduced terminal.

These modifications of glucose residues are not limited to the above, but can be carried out by other conventional methods. For example, methyl etherification can be replaced by lower alkylation such as ethyl etherification or isopropyl etherification or phenyl or substituted pheynl etherification such as phenyl etherification, p-nitrophenyl etherification, 2,4-dinitrophenyl etherification, p-aminophenyl etherification, 2,6-dibromo-4-aminophenyl etherification or 2,4-dichlorophenyl etherification; or acetylation can be replaced by propionylation, phosphorylation or $C_{5-20}$ esterification; or gluconic acid residues can be replaced by anhydrides such as those of the gluconolactone type. the syntheses of these glucose polymers are reported, for example, in U.S. Pat. Nos. 4,145,527 and 4,147,860, Jap. Unexam. Pat. Publ. No. 54-51892 and No. 57-68798. The degree of polymerization of glucose need not be limited to a uniform polymerization degree but may include various degrees of polymerization. Examples of cyclic glucose polymers are dextrins with more than six glucose units obtained from starches such as $\alpha$-, $\beta$-, $\gamma$-, $\delta$- or $\epsilon$-cyclodextrin.

Examples of enzymes which liberate saccharides, other than glycosidases such as amylase, are phosphatases and esterases. Examples of substrates for phosphatases such as alkali phosphatases, glucose-6-phosphatase, glucose-1-phosphatase or fructose-1,6-diphosphatase, are phosphorylated saccharides such as glucose-1-phosphate, glucose-1,6-diphosphate or fructose-1,6-diphosphate. These enzymes can be used for assaying an oxido-reductase which acts on phosphorylated saccharides, for example assaying the activity of glucose dehydrogenase by measuring remaining glucose-6-phosphate in an enzymatic reaction of glucose-6-phosphate dehydrogenase with substrate glucose-6-phosphate. Furthermore, these enzymes can be used for assaying kinase activity in the enzymatic synthesis of phosphorylated saccharides in the presence of ATP. Examples of substrates used for assaying esterase activity are $C_{5-20}$-acyl derivatives of saccharides. These substrates are hydrolyzed by a saccharide-liberating enzyme, for example a glucosidase such as amylase, phosphatase or esterase, in a sample at 37° C. buffered to pH 6–8 to form decomposed substrates such as glucose, maltose and other oligosaccharides such as maltotriose, maltotetraose, maltopentaose or maltohexaose.

Incubation time can be a time sufficient for liberating saccharides from the substrate and is usually more than one minute. The activity of saccharide-liberating enzymes such as glycosidase, an enzyme hydrolyzing glycoside linkages in sugar, can be assayed by measuring the decomposed substrate. The reaction can be conducted by incubating the decomposed substrate with maltose dehydrogenase (acceptor) and a hydrogen acceptor at 37° C. for more than 30 seconds, preferably for 1-60 minutes.

The quantitative determination of saccharide in a specimen can be performed by replacing the above decomposed substrate with a saccharide such as xylose, glucose, galactose, maltose, fructose, mannose, lactose, maltotriose, maltotetraose, maltopentaose, maltohexaose or maltoheptaose.

As hereinabove illustrated, substrate decomposed by the action of a saccharide-liberating enzyme, for example, α-amylase, β-amylase, a glycosidase such as α-glucosidase or glucoamylase, phosphatase or esterase, or saccharide to be assayed, is treated with maltose dehydrogenase in the presence of a hydrogen acceptor such as PMS, MPMS, 1-acetamide-phenazine methosulfate, meldola blue or 2,6-dichlorophenol indophenol to generate a reduced-form hydrogen acceptor.

The amount of hydrogen acceptor is 0.05-10 times excess as compared with the decomposed substrate or saccharide to be assayed. The reduced-form hydrogen acceptor can be measured, below an equi-molar amount thereof, by means of a cycling reaction system in which the reduced-form acceptor is regenerated to the hydrogen acceptor using a hydrogen transport reaction reagent in a reduced form, or oxygen. The preferred amount of maltose dehydrogenase (acceptor) is generally 0.01-100 U per test.

Thereafter a detectable change is measured, for example the thus-generated reduced-form hydrogen acceptor is quantitatively determined, which for this purpose is preferably reacted with a hydrogen transport system reaction reagent in reduced form to produce changes of absorbancy.

Examples of hydrogen transport reaction reagents in reduced form are, for example, tetrazolium salts such as 3-(p-iodophenyl)-2-(p-nitrophenyl)-5-phenyl -2H-tetrazolium chloride, 3-(4,5-dimethyl-2,4-azolyl)-2,5-diphenyl-2H-tetrazolium bromide, 3,3'-(4,4'-biphenylene)-bis(2,5-diphenyl-2H-tetrazolium chloride), 3,3'-(3,3'-dimethoxy-4,4'-biphenylene)-bis[2-(p-nitrophenyl)-5-phenyl-2H-tetrazolium chloride](nitrotetrazolium blue), 3,3'-(3,3'-dimethoxy-4,4'-biphenylene)-bis(2,5-diphenyl-2H-tetrazolium chloride), 2,6-dichlorophenolindophenol or methylene blue. These hydrogen transport reaction reagents in reduced form may be added in equimolar or excess amounts relative to the generated reduced-form hydrogen acceptor. The amount can be determined, depending on the time necessary for the cycling reaction for the hydrogen acceptor and the reaction time, and is preferably 10-1000 times the equimolar amount.

The resulting reaction product is colorimetrically measured. Alternatively, the reduced-hydrogen acceptor is reacted with dissolved oxygen and the amount of oxygen consumed can be measured by an oxygen electrode.

A specimen such as urine, saliva or blood is preferably pretreated with a hexose oxidase such as glucose oxidase and catalase, or with a kinase such as hexokinase, $Mg^{++}$ and ATP, in order to avoid the detrimental effect of glucose introducing an error in measurement. The said pretreatment can be performed simultaneously with the reaction with the glycosidase and the substrate. Glucose in the specimen can be removed by pre-treating the maltose dehydrogenase (acceptor) and the hydrogen acceptor with dissolved oxygen or bubbling oxygen or air.

In the accompanying drawings:

FIG. 1 shows the optimum pH of maltose dehydrogenase (acceptor);

FIG. 2 shows the optimum temperature of maltose dehydrogenase (acceptor);

FIG. 3 shows the pH-stability of maltose dehydrogenase (acceptor);

FIG. 4 shows the heat stability of maltose dehydrogenase (acceptor);

FIG. 5 shows the effect of substrate concentration of maltose dehydrogenase (acceptor);

FIGS. 9 and 10 show the results of assay of serum amylase using maltose dehydrogenase (acceptor);

FIG. 11 shows the results of assay of serum amylase using maltose dehydrogenase (acceptor);

FIG. 12 shows the results of assay of urine amylase using maltose dehydrogenase (acceptor);

FIG. 13 shows the electrophoretic pattern of serum amylase activity using maltose dehydrogenase (acceptor);

FIG. 17 shows the results of assay of human serum amylase using maltose dehydrogenase (acceptor).

Figure 8:
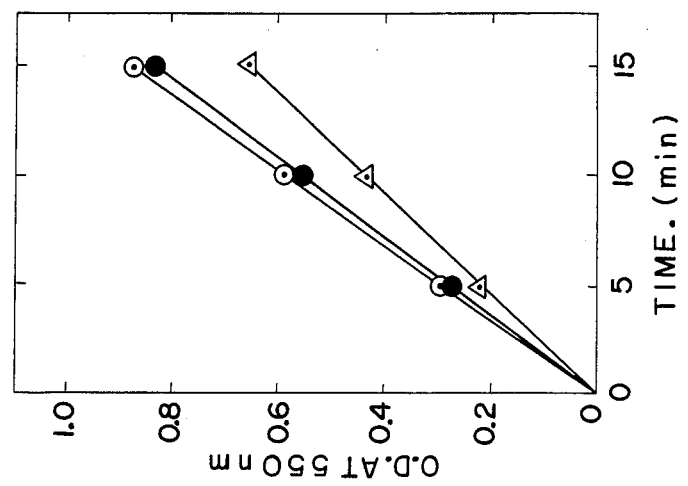
FIG. 8 shows the results of assay of urine amylase using maltose dehydrogenase (acceptor)

The following examples illustrate the present invention but are not to be construed as limiting:

EXAMPLE 1

One loopful of Staphylococcus sp. B-0875 FERM BP-385 from bouillon agar slant was inoculated in an aqueous medium (100 ml) comprising peptone 1.0%, bonito extract 1.0% and NaCl 0.3% (sterilized at 120° C. for 20 mins., pH 7.2) in a 500 ml Erlenmeyer flask, and the mixture was shake cultured at 28° C. for 24 hours. The thus-prepared seed culture was transferred into another aqueous medium (20 lit.) comprising peptone 1%, $K_2HPO_4$ 0.1%, NaCl 0.3%, $MgSO_4.7H_2O$ 0.1%, silicone SA G-471 (trademark, antifoamer) 0.1% (previously sterilized at 120° C. for 20 mins., pH 7.2) in a 30 lit. jar-fermenter (tank), and submerged cultured at 30° C. for 18 hours, 300 r.p.m., 20 lit./min. aeration. The cultured cells were collected by centrifugation at 5000 r.p.m. for 10 mins. The wet cells were treated with a solution of 0.1% lysozyme and 5 mM EDTA in phosphate buffer (pH 7.0, 1.5 lit.) at 37° C. for 60 mins. The solution of solubilized cells was centrifuged (5000 r.p.m., 10 mins.) to separate the supernatant (11.8 U/ml, 3.2 lit.) To the supernatant solution was added ammonium sulfate up to 28% of saturation and the mixture was centrifuged (5000 r.p.m., 20 mins.) and the supernatant solution collected. Further ammonium sulfate was added to the supernatant solution up to 72% of saturation. The precipitate was collected by centrifugation (5000 r.p.m., 20 mins.) and dissolved in 20 mM phosphate buffer (pH 7.0, 220 ml) and the mixture was centrifuged (15,000 r.p.m., 10 mins.) to obtain the supernatant solution (200 ml, 123.5 U/ml). The supernatant solution was dialyzed and charged on a column of CM-Sepharose CL-6B (bed vol. 80 ml) and eluted by gradient elution with KCl 0-0-.5 M to obtain the fraction containing maltose dehydrogenase (acceptor). This fraction was concentrated by an ultrafiltration membrane XM-30 (6 ml), purified by Sephacryl S-200 column chromatography, and desalted with a Sephadex G-25 column. The eluate in 1% sucrose solution was lyophilized to obtain the purified maltose dehydrogenase (acceptor) (160 mg, 38 U/mg).

EXAMPLE 2

80 mM Tris-HCl buffer pH 7.0
0.1% bovine serum albumin
0.05% nitrotetrazolium blue (NTB)
0.2 % Triton X-100
maltose dehydrogenase (acceptor) (10 U/ml)

Glucose, maltose, maltotriose, maltotetraose, maltopentaose and maltohexaose (20 μl, final concentration 0.05-0.25% (w/v)) were separately added to aliquots of the above reaction mixture in small test tubes, and these mixtures were incubated at 37° C. for 10 mins. After the reaction, 0.1N HCl (2 ml) was added to each and the mixtures were measured at 550 nm by colorimetry.

Figure 6:
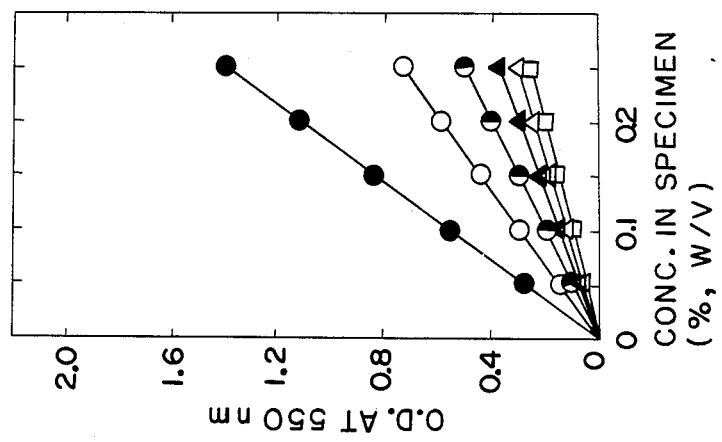
FIG. 6 shows the results of quantitative determination of mono- and oligosaccharides using maltose dehydrogenase (acceptor)

The results are shown in FIG. 6, wherein good linearity was obtained. In the figure: ●-●; glucose, o-o; maltose, ◐-◐; maltotriose, ▲-▲; maltotetraose, △-△; maltopentaose, □-□; maltohexaose.

EXAMPLE 3

Aliquots of the reaction mixture (each 1 ml), in which 5 mM p-nitrophenylpentaoside or p-nitrophenylheptaoside was added to the same reaction mixture described in Example 2, in small test tubes, were pre-incubated at 37° C. Aliquots of 500-fold-diluted saliva (a specimen containing amylase, 20 μl) were added thereto and the mixtures were incubated for 5, 10 and 15 mins., respectively.

Figure 7:
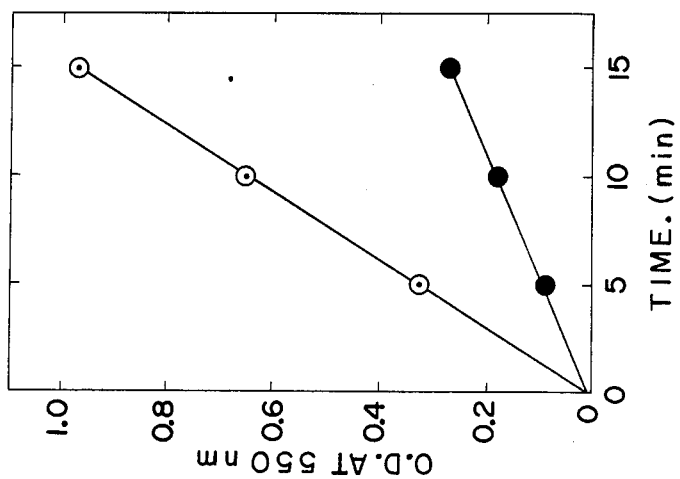
FIG. 7 shows the results of assay of salivary amylase activity using maltose dehydrogenase (acceptor)

The results are shown in FIG. 7, in which good quantitativity was obtained. Three times stronger activity was obtained for p-nitrophenylheptaoside as compared with p-nitrophenylpentaoside. No clear lag-time can be observed. In the figure: o-o; nitrophenylmaltoheptaose, ●-●; p-nitrophenylmaltopentaose.

EXAMPLE 4

Aliquots of the reaction mixture (each 1.0 ml), in which 5 mM p-nitrophenylheptaoside, methylheptaoside or β-gluconolactone heptaoside was added to the same reaction mixture described in Example 2, in small test tubes, were pre-incubated at 37° C. Human urine (20 μl) was added thereto and incubated for 5, 10 or 15 mins., respectively.

The results are shown in FIG. 8, in which good quantitativity was obtained. In the figure: o-o; p-nitrophenylmaltoheptaose, ●-●; 1-methylmaltoheptaose, △-△; δ-gluconolactone maltoheptaose.

EXAMPLE 5

50 mM phosphate buffer pH 7.5
0.1% serum albumin
0.2% Triton X-100
1% α-cyclodextrin
0.05% NTB
0.2 mM PMS
2 mM MgCl$_2$
hexokinase (25 U/ml)
2 mM ATP
maltose dehydrogenase (acceptor) (10 U/ml)
5 mM p-nitrophenyl maltoheptaose.

The above reaction mixture (1.0 ml) was introduced into a cuvette for spectrophotometry. Human serum (20 μl, amylase-containing specimen, 1/1, ¾, ½, ¼ dilution) was added thereto and the material was incubated at 37° C. and the changes in optical density were measured continuously at 550 nm.

The results are shown in FIG. 9. Changes of absorbancy in 2 mins. (from 5 to 7 mins.) are shown in FIG. 10 in which serum dilution is plotted in inverse proportion to absorbancy from optical density.

In FIG. 9: 1; without hexokinase, 2, 3, 4 and 5; serum dilution, 1/1, ¾, 2/4 and ¼, respectively. Solid line (1a-5a); no addition of p-nitrophenylamltoheptaose. Dashed line (1b-5b); addition of p-nitrophenylmaltoheptaose.

EXAMPLE 6

Reaction mixture I:
50 mM Tris-HCl buffer pH 7.0
glucose oxidase (100 U/ml)
catalase (1500 U/ml)
Reaction mixture II:
5 mM p-nitrophenylheptaoside added to the reaction mixture described in Example 2.

Serum (20 μl) was added to the reaction mixture I (0.2 ml) in a spectrophotometer cuvette, and the mixture was incubated at 37° C. for 5 mins. Changes of absorbancy from optical density were continuously recorded. The results are shown in FIG. 11 (2). Glucose oxidase was removed from the reaction system as a control which is shown in FIG. 11 (1).

EXAMPLE 7

40 mM BES buffer pH 7.0
0.02% PMS
5 mM p-nitrophenyl heptaoside

The reaction mixture hereinabove (1.0 ml) was introduced into a reaction vessel with an oxygen electrode and the mixture was pre-incubated at 37° C. Dilute human urine (⅛, ¼, ½, ¾, 1/1) was added thereto and the amylase activity in the urine was measured. The results are shown in FIG. 12, from which it will be seen that good quantitative results were obtained.

EXAMPLE 8 p-Nitrophenyl heptaoside was added to the reaction mixture described in Example 2, to a concentration of 5 mM. The solution thereof (20 μl) was introduced into a plate vessel. Electrophoresed serum on an agarose plate was immersed therein, and the active fraction was stained at room temperature for 30 mins., and then the reaction was stopped by immersing the plate in 0.1N HCl. The result is shown in FIG. 13, wherein the amylase activity can be seen to have been easily stained and the stained band shows clearly with no diffusion.

EXAMPLE 9

The methylated reducing terminal of dextrin (fraction above molecular weight 1000) of fructosyl-maltoheptaoside (G$_7$-fructose) was added to the reaction mixture described in Example 2 at 1% concentration.

α-Amylase (diluted human pancreatic juice, 0, 5, 10, 20, 30, 40 and 50 μl, respectively) was added to the reaction mixture hereinabove (10. ml) in a series of small test tubes, and these were incubated at 37° C. for 10 mins. The reaction was stopped by adding 0.1N HCl (2 ml) and the medium was colorimetrically measured at 550 nm.

Figure 14:
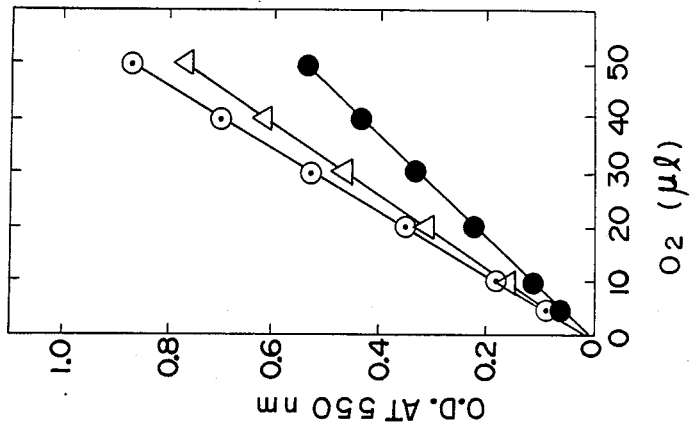
FIG. 14 shows the results of assay of amylase using maltose dehydrogenase (acceptor) or α-glucosidase.

The methylated dextrin was replaced by phenyl-α-D-glucopyranoside (2 mM) and after adding α-glucosidase (from yeast, Sigma Chem.) thereto, the same operation was repeated. Good linear relation of the amount of enzyme and absorbancy from optical density was obtained (FIG. 14). In the figure: o-o; $G_7$ fructose, Δ-Δ; methylated dextrin, ●-●; phenyl-α-D-glucopyranoside.

EXAMPLE 10

Figure 15:
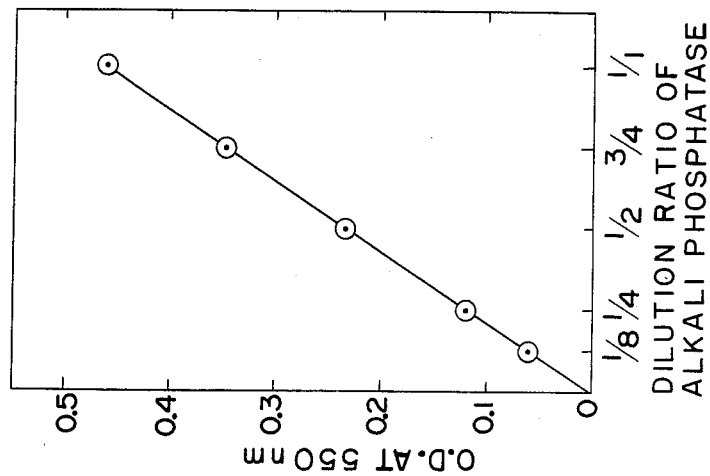
FIG. 15 shows the results of assay of alkali phosphatase using maltose dehydrogenase (acceptor)

In Example 2, the buffer solution in the reaction mixture and the substrate were replaced by 50 mM Tris-HCl buffer (pH 9.0) and 2 mM glucose-6-phosphate, respectively. The reaction mixture (1.0 ml) in a small test tube was pre-incubated at 37° C. An alkali phosphatase solution (10 μl, E. coli) was added thereto and the mixture was incubated at 37° C. for 10 mins. The reaction was stopped by adding 0.1N HCl (2.0 ml) and the material was colorimetrically measured at 550 nm. The results are shown in FIG. 15, from which it will be seen that good linearity was obtained.

EXAMPLE 11

Reaction mixture I:
 50 mM Tris-HCl buffer pH 7.0
 0.2 mM PMS
 maltose dehydrogenase (acceptor) (13 U/ml)
 2 mM $CaCl_2$
Reaction mixture II:
 50 mM Tris-HCl buffer pH 7.0
 2 mM NTB
 5.0 mM p-nitrophenyl heptaoside
 2 mM $CaCl_2$ Reaction mixture I (0.5 ml) in a spectrophotometer cell was pre-incubated at 37° C. Human serum or urine (20 μl) was added thereto and the mixture was incubated at 37° C. for 5 mins. Reaction mixture II pre-incubated at 37° C. (1.5 ml) was added thereto, and the changes of absorbancy at 550 nm were continuously measured at 37° C.

Figure 16:
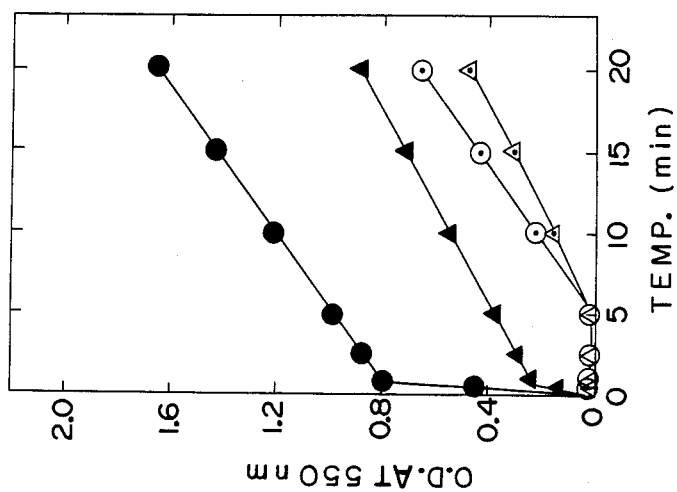
FIG. 16 shows the results of assay of human serum or urine amylase using maltose dehydrogenase (acceptor)

A control solution was prepared as follows:

The reaction mixture I (0.5 ml) and the reaction mixture II (1.5 ml) were mixed from the first stage, pre-incubated at 37° C., serum or urine (20 μl) was added, and the material was incubated at 37° C. The results are shown in FIG. 16, in which pre-treated solution with the reaction mixture I was shown to remove the effect of previously existing saccharides. In the figure: ●-●; serum control, o-o; pre-treated serum, ▲-▲; urine control, Δ-Δ; pre-treated urine.

EXAMPLE 12

Reaction mixture I:
 40 mM phosphate buffer pH 7.0
 33 mM ATP
 0.002% hydrogen acceptor
 4.17 mM $MgCl_2$
 maltose dehydrogenase (acceptor) (16.7 U/ml)
 hexokinase (11.7 U/ml)
Reaction mixture II:
 12.6 mM $CaCl_2$
 15.0 mM EDTA
 0.013% NTB
 0.5% Triton X-100
 2.5% reduced dextrin Human serun (20 μl) was added to the reaction mixture hereinabove (the hydrogen acceptor is shown in Table 6), and the material was incubated at 37° C. for 5 mins. Reaction mixture II (0.4 ml) was added thereto and the material was incubated at 37° C. Changes in absorbancy at 550 nm were measured. The results are shown in Table 6, from which it will be seen that serum amylase can be measured whatever the hydrogen acceptor.

TABLE 6

| Hydrogen Acceptor | Relative Amylase Activity |
|---|---|
| PMS | 100% |
| MPMS | 102% |
| 1-acetamidephenazine methosulfate | 103% |
| meldola blue | 97.4% |

EXAMPLE 13

Reaction mixture:
 40 mM phosphate buffer
 20 mM ATP
 2.5 mM $MgCl_2$
 hexokinase (5 U/ml)
 maltose dehydrogenase (acceptor, 10 U/ml)
 2% reduced dextrin
 0.2 mM 2,6-dichlorophenolindophenol The reaction mixture hereinabove (1.0 ml) in spectrophotometer cells was pre-incubated at 37° C. Human serum (5, 10, 20, 30 and 50 μ) was added thereto and the specimens were incubated at 37° C. for 5 mins. After completing the reaction, the changes of absorbancy at 600 nm were continuously measured. The results are shown in FIG. 17, from which it will be seen that good quantitativity was obtained.

What is claimed is:

1. An enzyme which acts on a reducing terminal of a monosaccharide or oligosaccharide without requiring NAD or NADP and which catalyzes the reaction $$R-O-\text{[glucose ring]}-OH + nA \longrightarrow$$

$$R-O-\text{[glucose ring]}=O + nAH \text{ or } AH_n$$

wherein R is a saccharide chain residue or hydrogen, A is a hydrogen acceptor other than NAD or NADP, AH or AHn is a reduced form acceptor and n is 1 or 2, said enzyme having greater substrate specificity on maltose than glucose.

2. An enzyme according to claim 1, wherein said hydrogen acceptor is a member selected from the group consisting of phenazine methosulfate, 1-methoxyphenazine methosulfate, meldola blue, 2,6-dichlorophenolindophenol and phenolindophenol.

3. An enzyme according to claim 1, wherein said enzyme is maltose dehydrogenase.

4. An enzyme according to claim 1, whose substrate is a member selected from the group consisting of maltose, glucose, xylose, mannose, galactose, fructose, lactose, maltotriose, maltotetraose, maltopentaose, maltohexaose and maltoheptaose, wherein said enzyme has the following physico-chemical and biochemical properties:
  molecular weight: 80,000±10,000
  isoelectric point: approximately pH 9.5
  Km value: approximately 3.8 mM (for maltose)
  optimum temperature: approximately 35° C.
  pH stability: stable at pH 7.5–8.5
  heat stbility: stable below 40° C.

5. A process for the production of maltose dehydrogenase which acts on a reducing terminal of a monosaccharide or oligosaccharide without requiring NAD or NADP and which catalyzes the reaction

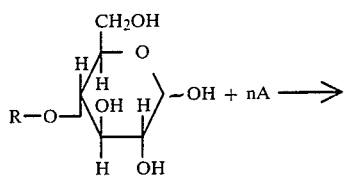

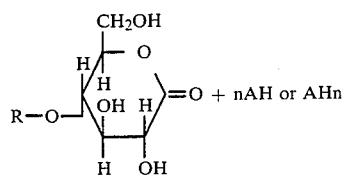

wherein R is a saccharide chain residue or hydrogen, A is a hydrogen acceptor other than NAD or NADP, AH or AHn is a reduced form acceptor and n is 1 or 2, said maltose dehydrogenase having greater substrate specificity on maltose than glucose, which comprises culturing a microorganism producing the said maltose dehydrogenase, said microorganism belonging to genus Staphylococcus, and isolating the thus-produced said maltose dehydrogenase from the culture medium.

6. A process according to claim 5, wherein said microorganism is Staphylococcus sp. B-0875 FERM BP-385.

7. An assay method for the determination of saccharide or the activity of a saccharide-liberating enzyme which acts on a substrate glucose derivative or glucose polymer, wherein maltose dehydrogenase does not act on the said substrate; said saccharide-liberating enzyme being selected from the group consisting of glycosidase, phosphatase and esterase, and liberating a decomposed substrate selected from the group consisting of maltose, glucose, xylose, mannose, galactose, fructose, lactose, maltotriose, maltotetraose, maltopentaose, maltohexaose and maltoheptaose upon acting on said substrate glucose derivative or glucose polymer, said method comprising reacting maltose dehydrogenase which catalyzes the reaction below, with a substrate in the presence of a hydrogen acceptor, and measuring the amount of a detectable change

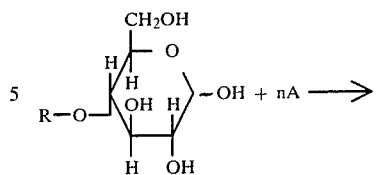

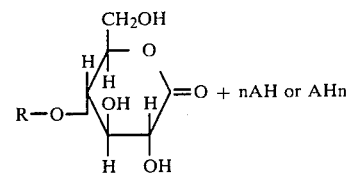

wherein R is a saccharide chain residue or hydrogen, A is a hydrogen acceptor other than NAD or NADP, AH or AHn is a reduced form acceptor and n is 1 or 2;
  substrate specificity of said maltose dehydrogenase: acts on maltose, glucose, xylose, mannose, galactose, fructose, lactose, maltotriose, maltotetraose, maltopentaose, maltohexaose or maltoheptaose, and substrate specificity on maltose is greater than that of glucose;
  hydrogen acceptor: phenazine methosulfate, 1-methoxy-phenazine methosulfate, meldola blue, 2,6-dichlorophenolindophenol or phenolindophenol.

8. An assay method according to claim 7, wherein said saccharide to be determined is a monosaccharide or oligosaccharide or a saccharide liberated by the action of a saccharide-liberating enzyme.

9. An assay method according to claim 1, wherein said glycosidase is a member selected from the group consisting of α-amylase, β-amylase, α-glycosidase and glucoamylase.

10. An assay method for the activity of a saccharide-liberating enzyme according to claim 7, wherein said saccharide-liberating enzyme activity is determined by assaying a decomposed substrate in which the substrate is a glucose polymer having a modified reducing terminal glucose residue or cyclic glucose polymer, by an enzymatic action using a glucose polymer having a modified reducing terminal glucose residue or cyclic glucose polymer.

11. An assay method for a saccharide-liberating enzyme according to claim 7, wherein said detectable change is measured by assaying the decomposed substrate by an enzymatic action using a monosaccharide, or an oligosaccharide having a modified reducing terminal, or an oligosaccharide which is not decomposed by said maltose dehydrogenase as a substrate.

12. An assay method according to claim 10, wherein the substrate is a glucose polymer having a modified reducing terminal glucose residue of amylose, amylopectin, starch or starch hydrolyzate.

13. An assay method according to claim 10, wherein the modified reducing terminal glucose residue is an etherified reducing terminal, an esterified reducing terminal, gluconolactone or a gluconic acid residue or a reduced form residue thereof.

14. An assay method according to claim 10, wherein the said assay is performed by measuring the amount of generated reduced-form hydrogen acceptor.

15. An assay method according to claim 10, wherein the said assay is performed by measuring the changes of absorbancy which result from reacting a reduced-form hydrogen acceptor with a reduced-form hydrogen transport colorimetric reaction reagent for said acceptor.

16. An assay method according to claim 14, wherein said measuring of a reduced-form hydrogen acceptor is performed by reacting tbhe reduced-form hydrogen acceptor with dissolved oxygen and the amount of oxygen consumed is measured using an oxygen electrode.

17. An assay method according to claim 15, wherein said reduced-form hydrogen transport colorimetric reaction reagent is a tetrazolium salt, 2,6-dichlorophenolindophenol or methylene blue.

18. An assay method for an activity of saccharide-liberating enzyme is a specimen according to claim 7, wherein glycosidase activity is determined by previously or simultaneously treating the specimen with hexose oxidase and catalase.

19. An assay method according to claim 18, wherein said hexose oxidase is a glucose oxidase.

20. An assay method according to claim 7, wherein the activity of said saccharide-liberating enzyme is determined by previously or simultaneously treating the specimen with hexokinase in the presence of $Mg^{++}$ and ATP.

21. An assay method according to claim 7, wherein the activity of said saccharide-liberating enzyme in a specimen is determined after pre-treating the specimen with said maltose dehydrogenase in the presence of an oxygen acceptor and a hydrogen acceptor.

22. An assay method according to claim 7, wherein said maltose dehydrogenase has the following properties:
molecular weight: 80,000±10,000
isoelectric point: approximately pH 9.5
Km value: approximately 3.8 mM (for maltose)
optimum temperature: approximately 35° C.
pH stability: stable pH 7.5–8.5
heat stability: stable below 40° C.

* * * * *